(12) United States Patent
Iwakura et al.

(10) Patent No.: US 6,706,910 B2
(45) Date of Patent: Mar. 16, 2004

(54) METHOD FOR PRODUCING CYCLOPROPANECARBOXYLATES

(75) Inventors: Kazunori Iwakura, Ibaraki (JP); Hiroshi Souda, Takatsuki (JP); Tohei Takagaki, Misawa (JP); Yoshimi Yamada, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 181 days.

(21) Appl. No.: 09/984,894

(22) Filed: Oct. 31, 2001

(65) Prior Publication Data

US 2002/0052525 A1 May 2, 2002

(30) Foreign Application Priority Data

Nov. 1, 2000 (JP) ........................... 2000-334375
Nov. 29, 2000 (JP) ........................... 2000-362494

(51) Int. Cl.⁷ .............................................. C07C 69/74
(52) U.S. Cl. ....................................... 560/124; 560/234
(58) Field of Search ................................ 560/124, 234

(56) References Cited

U.S. PATENT DOCUMENTS

| | | |
|---|---|---|
| 6,008,404 A | 12/1999 | Miller et al. |
| 6,225,495 B1 | 5/2001 | Ujihara et al. |

FOREIGN PATENT DOCUMENTS

| | | | |
|---|---|---|---|
| EP | 0 926 129 A1 | 6/1999 | |
| EP | 0 992 479 A1 | 4/2000 | |
| EP | 0992479 A1 | 4/2000 | |
| EP | 1 004 569 A1 | 5/2000 | |
| EP | 1 061 065 A2 | 12/2000 | |
| FR | 2 348 192 | 11/1977 | |
| GB | 1571388 | * | 7/1980 |
| JP | 52128336 | | 10/1977 |
| JP | 52-128336 | * | 10/1977 |

OTHER PUBLICATIONS

Gazette of Patents and Trademarks, (HU P9102429 A), May 28, 1993.

* cited by examiner

Primary Examiner—Alan L. Rotman
Assistant Examiner—Hector M Reyes
(74) Attorney, Agent, or Firm—Birch, Stewart, Kolasch & Birch, LLP

(57) ABSTRACT

There is provided a method for producing a cyclopropanecarboxylate of formula (1):

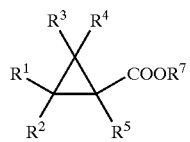

(1)

which comprises contacting
a cyclopropanecarboxylate of formula (2):

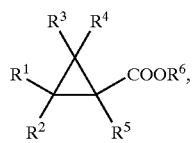

(2)

with a monohydroxy compound of formula (3):

$$R^7OH \qquad (3)$$

in the presence of a lithium compound of formula (4):

$$R^8OLi \qquad (4),$$

wherein $R^1$, $R^2$, $R^3$, $R^4$ and $R^5$ each independently represent
  a hydrogen atom, a halogen atom,
  a substituted or unsubstituted alkyl group,
  a substituted or unsubstituted alkenyl group, or
  a substituted or unsubstituted aryl group;
$R^6$ represents an alkyl group having 1 to 10 carbon atoms or
  a substituted or unsubstituted phenyl group;
$R^7$ and $R^8$ do not simultaneously represent the same and each independently represent
  a substituted or unsubstituted alkyl group, or
  a substituted or unsubstituted aryl group.

16 Claims, No Drawings

METHOD FOR PRODUCING CYCLOPROPANECARBOXYLATES

FIELD OF THE INVENTION

The present invention relates to a method for producing a cyclopropanecarboxylate.

BACKGROUND OF THE INVENTION

A method for producing a cyclopropanecarboxylic acid ester by transesterification reaction employing a sodium alkoxide catalyst has been disclosed (JP-A-52-128336).

However, said transesterification reaction has not been always satisfactory as an industrial production process in that the reaction is accompanied by various by-products and the obtained ester is colored.

SUMMARY OF THE INVENTION

According to the present invention, a cyclopropanecarboxylate can be readily obtained in an industrially desirable manner by conducting a transesterification reaction between a cyclopropanecarboxylate and a monohydroxy compound in the presence of a lithium compound as described below.

The present invention provides
a method for producing a cyclopropanecarboxylate of formula (1):

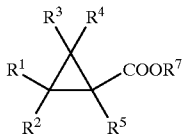

(1)

which comprises contacting
a cyclopropanecarboxylate of formula (2):

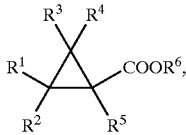

(2)

with a monohydroxy compound of formula (3):

 (3), in the presence of a lithium compound of formula (4):

 (4), wherein $R^1$, $R^2$, $R^3$, $R^4$ and $R^5$ each independently represent
a hydrogen atom, a halogen atom,
a substituted or unsubstituted alkyl group,
a substituted or unsubstituted alkenyl group, or
a substituted or unsubstituted aryl group;
$R^6$ represents an alkyl group having 1 to 10 carbon atoms or a substituted or unsubstituted phenyl group;
$R^7$ and $R^8$ do not simultaneously represent the same and each independently represent
a substituted or unsubstituted alkyl group, or
a substituted or unsubstituted aryl group.

DETAILED DESCRIPTION OF THE INVENTION $R^1$, $R^2$, $R^3$, $R^4$ and $R^5$ in the cyclopropanecarboxylate of formula (1) or (2) each will be explained below.

Examples of the substituted or unsubstituted alkyl group includes, for example, a substituted or unsubstituted straight, branched or cyclic alkyl group having 1 to 10 carbon atoms, which may be optionally substituted with a group selected from
   a halogen atom (e.g., fluorine, chlorine, bromine, or idodine),
   a (C1–C3)alkoxy group (e.g. methoxy, ethoxy, n-propoxy, i-propoxy),
   a (C1–C5)alkoxylcarbonyl group (e.g. methoxycarbonyl, ethoxycarbonyl, n-propoxycarbonyl, i-propoxycarbonyl, n-butoxycarbonyl, s-butoxycarbonyl, i-butoxycarbonyl, t-butoxycarbonyl, n-pentyloxycarbonyl and the like),
   a (C1–C5)alkylsulfonyl group(e.g. methylsulfonyl, ethylsulfonyl, n-propylsulfonyl, n-butylsulfonyl, n-pentylsulfonyl and the like),
   a (C1–C5)alkylsulfonyloxy group(e.g. methylsulfonyloxy, ethylsulfonxyloxy, n-propylsulfonyloxy, n-butylsulfonyloxy, n-pentylsulfonyloxy and the like),
   a (C1–C3)alkoxyimino group (e.g., methoxyimino, ethoxyimino, propyloxyomino, and the like), and
   a hydroxysulfenyl group.

Specific examples thereof include, for example, methyl, ethyl, n-propyl, i-propyl, n-butyl, sec-butyl, tert-butyl, n-pentyl, n-hexyl, n-heptyl, n-octyl, n-nonyl, n-decyl, cyclohexyl, menthyl, chloromethyl, dichloromethyl, trichloromethyl, bromomethyl, dibromomethyl, tribromomethyl, 1-chloroethyl, 2-chloroethyl, 1-bromoethyl, 2-bromoethyl, 1,2-dichloroethyl, 1,2-dibromoethyl, 2,2,2-trichloroethyl, 2,2,2-tribromoethyl, methoxymethyl, 2-methoxyethyl, and the like.

In addition, examples of the substituted alkyl group include, for example, a phenyl- or naphthyl-substituted (C1–C2)alkyl group which may be optionally substituted, on the phenyl or naphthyl ring, with a group selected from
   a (C1–C10)alkyl group, which may be substituted with a halogen atom,
   a (C1–C6)alkoxy group, which may be substituted with a halogen atom (e.g., methoxy, ethoxy, n-propoxy, i-propoxy, n-butoxy, sec-butoxy, t-butoxy, cyclohexloxy and the like), and
   a halogen atom.

Specific examples thereof include a benzyl, diphenylmethyl, phenylethyl, naphthylmethyl, naphthylethyl group and the like.

Specific examples of the (C1–C10)alkyl group can be referred to below in the present specification.

Examples of the substituted or unsubstituted alkenyl group include, for example,
   a (C2–C5)alkenyl group optionally substituted with a group selected from a halogen atom,
   a phenyl group,
   a (C1–C5)alkoxycarbonyl group, which may be substituted with a halogen atom,
   a (C1–C5)alkylsulfonyl group,
   a (C1–C3)alkylsulfonyloxy group, and
   a (C1–C3)alkoxyimino group.

Specific examples thereof include, for example, vinyl, 1-methylvinyl, 1-propenyl, 2-methyl-1-propenyl, 1-butenyl, 2-butenyl, 3-methyl-2 -butenyl, 2,2-dichlorovinyl, 2,2-dibromovinyl, 2-chloro-2-fluorovinyl, 2-chloro-2-trifluoromethylvinyl, 2-bromo-2-tribromomethylvinyl, 2,2-difluorocyclopropylidenemethyl and the like.

Examples of the substituted or unsubstituted aryl group include, for example, a phenyl or naphthyl group which may be optionally substituted with the above-described (C1–C10)alkyl group, a (C1–C10)alkoxy group or a halogen atom and the like.

Specific examples thereof include, for example, phenyl, 1-naphthyl, 2-naphthyl and the like.

$R^6$ in formula (2) will be explained below.

The alkyl group having 1 to 10 carbon atoms may be straight, branched or cyclic, and examples thereof include, for example, methyl, ethyl, n-propyl, i-propyl, n-butyl, sec-butyl, tert-butyl, n-pentyl, n-hexyl, cyclohexyl, n-heptyl, n-octyl, n-nonyl, n-decyl, menthyl and the like. Methyl and ethyl are preferred. Examples of the (C1–C10)alkoxy group, disclosed in the present specification, include, for example, an alkoxy group having the above-described alkyl group and oxygen atom.

The phenyl group may be optionally substituted with a group selected from a (C1–C10)alkyl group, a (C1–C10) alkoxy group, a halogen atom and the like.

Specific examples of the cyclopropanecarboxylate of formula (2) include, for example, methyl cyclopropanecarboxylate,
methyl 2-fluorocyclopropanecarboxylate,
methyl 2,2-dichlorocyclopropanecarboxylate,
methyl 2,2-dimethyl-3-(dimethoxymethyl) cyclopropanecarboxylate,
methyl 2,2-dimethyl-3-(dimethoxymethyl) cyclopropanecarboxylate,
methyl 2,2,3,3-tetramethylcyclopropanecarboxylate,
methyl 2,2-dimethyl-3-(1-propenyl) cyclopropanecarboxylate,
methyl 2,2-dimethyl-3-(2-methyl-1-propenyl) cyclopropanecarboxylate,
methyl 2,2-dimethyl-3-(1-butenyl)cyclopropanecarboxylate
methyl 2,2-dimethyl-3-(3-methyl-2-butenyl) cyclopropanecarboxylate,
methyl 2,2-dimethyl-3-(2,2-dichlorovinyl) cyclopropanecarboxylate,
methyl 2,2-dimethyl-3-(2,2,2-trichloroethyl) cyclopropanecarboxylate,
methyl 2,2-dimethyl-3-(2-chloro-2 -fluorovinyl) cyclopropanecarboxylate ,
methyl 2,2-dimethyl-3-(2-bromovinyl) cyclopropanecarboxylate,
methyl 2,2-dimethyl-3-(2,2-dibromovinyl) cyclopropanecarboxylate,
methyl 2,2-dimethyl-3-(1,2,2,2-tetrabromoethyl) cyclopropanecarboxylate,
methyl 2,2-dimethyl-3-(1,2-dibromo-2,2-dichloroethyl) cyclopropane-carboxylate,
methyl 2,2-dimethyl-3-(2-chloro-3,3,3-trifluoro-1-propenyl)cyclopropane-carboxylate,
methyl 2,2-dimethyl-3-{3,3,3-trifluoro-2-(trifluoromethyl)-1-propenyl}-cyclopropanecarboxylate,
methyl 2,2-dimethyl-3-(2-phenyl-1-propenyl) cyclopropanecarboxylate,
methyl 2,2-dimethyl-3-(2-phenylvinyl) cyclopropanecarboxylate,
methyl 2,2-dimethyl-3-(2-methyl-3-phenyl-2-butenyl) cyclopropanecarboxylate,
methyl 2,2-dimethyl-3-{(2,2-difluorocylopropylidene) methyl}cyclopropanecarboxylate,
methyl 2,2-dimethyl-3-{2-(t-butoxycarbonyl) vinyl}cyclopropanecarboxylate,
methyl 2,2-dimethyl-3-{2-fluoro-2-(methoxycarbonyl) vinyl}cyclopropanecarboxylate,
methyl 2,2-dimethyl-3-{2-fluoro-2-(ethoxycarbonyl) vinyl}cyclopropanecarboxylate,
methyl 2,2-dimethyl-3-{2-fluoro-2-(t-butoxycarbonyl) vinyl}cyclopropanecarboxylate,
methyl 2,2-dimethyl-3-[2-{2,2,2-trifluoro-1-(trifluoromethyl)ethoxycarbonyl}-vinyl] cyclopropanecarboxylate,
methyl 2,2-dimethyl3-(2-aza-2-methoxyvinyl) cyclopropanecarboxylate,
methyl 2,2-dimethyl-3-(2-aza-2-ethoxyvinyl) cyclopropanecarboxylate,
methyl 2,2-(dimethyl-3-(4-aza-4-methoxy-3-methylbuta-1,3-dienyl)-cyclopropanecarboxylate,
methyl 2,2-dimethyl-3-[2-{(t-butyl)sulfonyl}-2-(t-butoxycarbonyl)vinyl]-cyclopropanecarboxylate,
methyl 2,2-dimethyl-3-{2,2,2-tribromo-1-(methylsulfonyloxy)ethyl}-cyclopropanecarboxylate,
methyl 2,2-dimethyl-3-{2,2-dibromo-2-(hydroxysulfinyl)-1-(methoxy)ethyl}-cyclopropanecarboxylate,
methyl 2,2-dimethyl-3-{2-(t-butylsulfonyl)-2-(t-butoxycarbonyl)-ethyl}cyclopropanecarboxylate,
methyl 2,2-dimethyl-3-{2,2,2-tribromo-1-(methylsulfonyloxy)ethyl}-cyclopropanecarboxylate,
methyl 2-methyl-2-ethyl-3-(1-propenyl) cyclopropanecarboxylate,
methyl 2,2-diethyl-3-(2,2-dichlorovinyl) cyclopropanecarboxylate,
methyl 2-methyl-2-phenyl-3-(2-methyl-1-propenyl) cyclopropanecarboxylate and those esters having an ethyl group, a butyl group, a menthyl group or the like in place of the methyl residue in any of the methyl cyclopropanecarboxylates above.

Preferred carboxylic acid esters include, for example, a carboxylate of formula (2), wherein $R^1$ represents a methyl group, or a C3 to C4 alkenyl group (e.g. a 2-methyl-1-propenyl group, a 1-propenyl group or the like), $R^2$ represents a hydrogen atom, or a methyl group, $R^3$ and $R^4$ represent a methyl group, $R^5$ represents a hydrogen atom, $R^6$ represents a methyl group or an ethyl group. Such a carboxylate ester is preferably used with the monohydroxy compound of formula (5) as defined below.

Particularly preferred esters include, for example, 2,2-dimethyl-3-(1-propenyl)cyclopropanecarboxylate and 2,2-dimethyl-3-(2-methyl-1-propenyl) cyclopropanecarboxylate.

$R^7$ in the monohydroxy compound of the formula (3) in the present invention will be explained below.

The substituted or unsubstituted alkyl group include, for example,
 a (C1–C10)alkyl group which may be substituted with a
  group selected from:
   a halogen atom,
   a (C3–C4)alkenyl group which may be substituted with
    a halogen atom,
   a (C3–C4)alkynyl group,
   a (C5–C6)cycloalkyl group (e.g. cyclopentyl or cyclohexyl),
   a (C5–C6)cycloalkenyl group (e.g. cyclopentenyl or cyclohexenyl group),
   a heterocyclic group selected from:
    a furyl group which may be substituted with a phenoxy group, a benzyl group, difluoromethyl group or a propynyl group, a pyrrolyl group substituted with a propynyl group and optionally with a halomethyl group, a thiazolyl group substituted with a halomethyl group or a halomethoxy group, an isoxazolyl group optionally substituted with a methyl group, a 4,5,6,7-tetrahydroisoindol-1,3-dione-2-yl group, a 1-propynyl-imidazolidine-2,4-dione-3-yl group, a pyrazolyl group substituted with a propyne group and a halomethyl group, a halo-pyridyl group, a thiazolin-2-one-5-yl group substituted with a methyl group and a propynyl group, and a 1-prop-2-ynylindol-3-yl group substituted with a methyl or trihalomethyl group;

a (C5–C6)oxocycloalkenyl group substituted with a methyl group and either a propenyl group or a propynyl group. A preferred group in the (C1–C10)alkyl group is a methyl group.

Examples of the substituted alkyl group also include, for example, a substituted or unsubstituted (C6–C18)aralkyl group such as a phenyl-, naphthyl-, or anthracenyl-substituted (C1–C4)alkyl group, which phenyl-, naphthyl-, or anthracenyl group may be optionally substituted with a group selected from:

a nitro group, a cyano group, a halogen atom, a (C1–C14)alkyl group which may be substituted with a halogen atom, a (C1–C3)alkoxy group which may be substituted with a halogen atom, a (C1–C4)alkoxy(C1–C3)alkyl group which may be substituted with a halogen atom, a (C2–C3)alkenyl group which may be substituted with a halogen atom, a (3–C5)alkynyl group, a haloacetyloxy(C1–C3)alkyl group, a (C1–3)alkylthio group which may be substituted with a halogen atom, an amino group, a thienyl group, a phenyl group, and a phenoxy group which may be substituted with a halogen atom, and said (C1–C4)alkyl group may form a indanyl group with the phenyl group.

The substituted or unsubstituted aryl group include, for example, a phenyl or naphthyl group which may be optionally substituted with a group selected from a halogen atom, a (C1–C10)alkyl group, a (C1–C10)alkoxy group, a (C3–C5)alkynyl group, an acetyl group, an aldehyde group and the like.

Examples of the monohydroxy compound of the formula (3) include, for example, a substituted or unsubstituted alkyl, aralkyl or aryl alcohol, wherein said alkyl, aralkyl, and aryl groups are the same as defined above.

Examples of the substituted or unsubstituted alkyl alcohol include:

a (C1–C10)alkyl alcohol compound or a halo(C1–C10) alkyl alcohol such as methyl alcohol, ethyl alcohol, n-propyl alcohol, i-propyl alcohol, n-butyl alcohol, sec-butyl alcohol, tert-butyl alcohol, n-pentyl alcohol neopentyl alcohol, amyl alcohol, n-hexyl alcohol, n-octyl alcohol, n-nonyl alcohol, n-decyl alcohol, fluoroethyl alcohol, trifluoroethyl alcohol, 3,3-dibromo-2-propen-1-ol, hexafluoroisopropyl alcohol, perfluorobutyl alcohol, perfluoropentyl alcohol, perfluorohexyl alcohol, perfluorooctyl alcohol, perfluorodecyl alcohol or the like;

a (C1–C10)alkyl alcohol substituted with a heterocyclic group as defined above such as 2-furylmethyl alcohol, 3-furylmethyl alcohol, (5-phenoxy-3-furyl)methyl alcohol, (5-benzyl-3-furyl)methane-1-ol,

[5-(difluoromethyl)-3-furyl]methane-1-ol, 5-propargyl-2-furfuryl alcohol, (5-methylisoxazol-3-yl)methane-1-ol, 1-[2-(trifluoroimethyl)-1,3-thiazol-4-yl]prop-2-yn-1-ol, 1 [-2-(trifluoromethoxy)-1,3-thiazol-4-yl]prop-2-yn 1-ol, 1-[1-prop -2-ynyl-5-(trifluoromethyl)pyrrol-3-yl]prop-2-yn-1-ol, (1-prop-2-ynylpryrrol-3-yl)methan-1-ol, 3-(hydroxymethyl)-1-propynyl-imidazolydine-2,4-dione, 2-(hydroxymethyl)-4,5,6,7-tetrahydroisoindole-1,3-dione,

[1-(2-propynyl)pyrrol-3-yl]methan-1-ol, 5-(hydroxymethyl)-4-methyl-(2-propynyl)-1,3 -thiazolin-2-one,

[1-(2-propynyl)-5-(trifluoromethyl-4-pyrazolyl]methan-1-ol, (1-prop-2-ynyl-2-methylindol-3-yl)methane-1-ol,

[1-prop-2-ynyl-2-(trifluoromethyl)indol-3 -yl]methane-1-ol, or (2,3,6-trichloro-4-pyridyl)methane-1-ol;

a (C1–C10)alkyl group which may be substituted with a (C3–C4)alkenyl group, which alkenyl group may be substituted with a halogen atom, or a (C3–C4)alkynyl group such as 4-fluorohept-4-en-1-yn-3-ol, or 4-methylhept-4-en-1-yn-3-ol; and a (C5–C6)oxocycloalkenyl group substituted with a methyl group and either a propenyl group or a propynyl group such as 4-hydroxy-3-methyl-2-(2-propenyl)-2-cyclopentene-1-one, or 4-hydroxy-3-methyl-2-(2-propynyl)-2-cyclopentene-1-one.

In the substituted or unsubstituted alkyl group of the alcohol compound of formula (2), preferred are substituted alkyl groups.

Examples of the substituted or unsubstituted aralkyl alcohol include; benzyl alcohol, 2-methyl-3 -phenylbenzyl alcohol, 2,3,5, 6-tetrafluorobenzyl alcohol, 2,3,4,5,6-pentafluorobenzyl alcohol, 2,3,5,6-tetrafluoro-4-(methoxymethyl)benzyl alcohol, 2,3,5,6-tetrafluoro-4-methoxybenzyl alcohol, 2,3,5,6-tetrafluoro-4-chlorobenzyl alcohol, 2,3,5,6-tetrafluoro-4-bromobenzyl alcohol, 2,3,5,6-tetrafluoro-4-trifluoromethylbenzyl alcohol, 2,3,5,6-tetrafluoro-4-difluoromethylbenzyl alcohol, 2,3,5,6-tetrafluoro-4-methylbenzyl alcohol, 2,3,5,6-tetrafluoro-4-vinylbenzyl alcohol, 2,3,5,6-tetrafluoro-4-allylbenzyl alcohol, 2,3,5,6-tetrafluoro-4-(2,2-dichlorovinyl)benzyl alcohol 2,3,5,6-tetrafluoro-4-difluoromethoxybenzyl alcohol 2,3,5,6-tetrafluoro-4-trifluoronethoxybenzyl alcohol 2,3,5,6-tetrafluoro-4-methylthiobenzyl alcohol 2,3,5,6-tetrachlorobenzyl alcohol, 2,3,5,6-tetrachloro-4-methylbenzyl alcohol, 2,3,5,6-tetrachloro-4-methoxybenzyl alcohol, 2,3,5,6-tetrachloro-4-methoxymethylbenzyl alcohol, 2,3,5,6-tetrachloro-4-propargylbenzyl alcohol, 2,3,5,6-tetrachloro-4-dichloromethylbenzyl alcohol, 2,3,5,6-tetrachloro-4-dichloromnethoxylbenzyl alcohol, 2,3,5,6-tetrachloro-4-(2,2,2-trichloroacetyloxymethyl) benzyl alcohol 2,3,5,6-tetrachloro-4-dichloromethoxylbenzyl alcohol 4-trichloromethylbenyl alcohol,
2,3,4,5-tetrachloro-6-methylbenzyl alcohol,
6-chloro-2,3,4-trifluoromethylbenzyl alcohol,
2-chloro-3,6-difluorobenzyl alcohol,
4-(trifluoromethyl)benzyl alcohol,
3-phenylbenzyl alcohol 2,6-dichlorobenzyl alcohol,
3-phenoxybenzyl alcohol,
2-hydroxy-2-(3-phenoxyphenyl)ethanenitrile,
2-hydroxy-2-[4-(methoxymethyl)phenyl]ethanenitrile,
2-[3-(4-chlorophenoxy)phenyl]-2-hydroxyethanenitrile,
2-(4-amino-2,3,5,6-tetrafluorophenyl)-2-hydroxyethanenitrile,
2-(4-chloro-3-phenoxyphenyl)-2-hydroxeythanenitrile,
(2-methylphenyl)methyl alcohol,
(3-methylphenyl)methyl alcohol,
(4-methylphenyl)methyl alcohol,
(2,3-dimethylphenyl)methyl alcohol,
(2,4-dimethylphenyl)methyl alcohol,
(2,5-dimethylphenylmethyl alcohol,
(2,6-dimethylphenyl)methyl alcohol,
(3,4-dimethylphenyl)methyl alcohol,
(2,3,4-trimethylphenyl)methyl alcohol,
(2,3,5-trimethylphenyl)methyl alcohol,
(2,3,6-trimethylphenyl)methyl alcohol,
(3,4,5-trimethylphenyl)methyl alcohol,
(2,4,6-trimethylphenyl)methyl alcohol,
(2,3,4,5-tetramethylphenyl)methyl alcohol,
(2,3,4,6-tetramethylphenyl)methyl alcohol,
(2,3,5,6-tetramethylphenyl)methyl alcohol,
(pentamethylphenyl)methyl alcohol,
(ethylphenyl)methyl alcohol,
(n-propylphenyl)methyl alcohol,
(i-propylphenyl)methyl alcohol,
(n-butylphenyl)methyl alcohol,
(sec-butylphenyl)methyl alcohol,
(tert-butylphenyl)methyl alcohol,
(n-pentylphenyl)methyl alcohol,
(neopentylphenyl)methyl alcohol,
(n-hexylphenyl)methyl alcohol,
(n-octylphenyl)methyl alcohol,
(n-decylphenyl)methyl alcohol,
(n-dodecylphenyl)methyl alcohol,
(n-tetradecylphenyl)methyl alcohol, naphthylmethyl alcohol,
anthracenylmethyl alcohol, 1-phenylethyl alcohol,
1-(1-naphthyl)ethyl alcohol, 1-(2-naphtyl)ethyl alcohol,
(4-prop-2-ynylphenyl)methane-1-ol,
(3-prop-2-ynylphenyl)methane 1 -ol,
4-prop-2-enylindane-1-ol 4-phenylindane-2-ol, and
4-(2-thienyl)indane-2-ol.

Examples of the substituted unsubstituted aryl alcohol include phenol, 1-naphthol, 2-naphthol, 4-prop-2-ynylphenol, 3-prop-2-ynylphenol, 4-hydroxyacetophenone, 4-hydroxybenzaldehyde and the like, and aryl alcohol compounds substituted with a (C1–C10)alkyl group, a (C1–C10) alkoxy group or halogen atom and the like on the aromatic ring.

Among the alcohol compound of the formula (3), a primary alcohol is preferred and a further preferred alcohol is an alcohol wherein $R^7$ group is a substituted or unsubstituted aralkyl group. Examples of the preferred group include, for example, a phenylmethyl(benzyl) group, which phenyl group may be optionally substituted with a group selected from:
  a halogen atom,
  a (C1–C14)alkyl group which may be substituted with a halogen atom,
  a (C1–C3)alkoxy group which may be substituted with a halogen atom,
  a (C1–C4)alkoxy(C1–C3)alkyl group which may be substituted with a halogen atom,
  a (C2–C3) alkenyl group which may be substituted with a halogen atom,
  a (C3–C5)alkynyl group, a haloacetyloxy(C1–C3)alkyl group,
  a (C1–C3) alkoxy group which may be substituted with a halogen atom,
  an amino group, a thienyl group, a phenyl group, and a phenoxy group which may be substituted with a halogen atom.

More preferred benzyl alcohol compounds include, for example, a benzyl alcohol compound of formula (5):

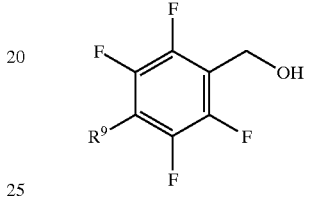

(5)

wherein $R^9$ represents a hydrogen atom, a halogen atom,
a (C1–C3) alkyl which may be substituted with a halogen atom,
a (C2–C3) alkenyl group which may be substituted with a halogen atom,
a (C1–C3) alkoxy group which may be substituted with a halogen atom,
a (C1–C3) alkylthio group which may be substituted with a halogen atom, or
a (C1–C4)alkoxymethyl group which lay be substituted with a halogen atom.

Further more preferred alcohols include, for example, 3-phenoxybenzyl alcohol, 2,3,5,6-tetrafluorobenzyl alcohol, and
2,3,5,6-tetrafluoro4-methoxybenzylalcohol.

Any amount of the monohydroxy compound (3) may be used, and the amount is typically, for example, one mole or more, preferably 1 to 3 moles, more preferably 1 to 2 moles per mole of the cyclopropanecarboxylate (2) and also it may be used in excess amount or can be used as a solvent. The monohydroxy compound (3) in the reaction mixture can be recovered by, for example, an operation such as distillation and the like after completion of the reaction. Alternatively, the amount of the monohydroxy compound (3) may be not more than one mole per mole of the cyclopropanecarboxylate (2), and an appropriate operation as above may be conducted with a cyclopropanecarboxylate (2) in the reaction mixture after completion of the reaction.

Examples of the lithium compound of formula (4) include, for example, lithium salt of the mono-hydroxy compound of formula (3) as described above and lithium.

The group represented by $R^8$ in the lithium compound of formula (4) has the same meaning as defined for $R^7$ above, wherein $R^8$ is not the same as $R^7$.

Preferred lithium compounds of formula (4) include, for example, a lithium alkoxide having 1 to 4 carbon atoms such as lithium methoxide, lithium ethoxide, lithium n-propoxide, lithium i-propoxide, lithium t-butoxide, or the like, lithium benzyloxide, lithium phenoxide and the like. More preferred are readily available and inexpensive lithium methoxide, lithium ethoxide and the like.

The lithium compound of formula (4) may be commercially available or it may be prepared from the monohydroxy compound of formula (3) and lithium metal, lithium hydride, or alkyl lithium. The lithium compound may be prepared and isolated prior to the transesterification reaction or the lithium compound thus prepared may be used as it is without being isolated, and it may be prepared in the transesterification reaction mixture, Any amount of lithium compound may be used in the present reaction, and it is usually about 0.001 to about 200 mole %, preferably 0.1 to 10 mole % per mol of the cyclopropanecarboxylate of formula (2).

The reaction of cyclopropanecarboxylate (1) with the monohydroxy compound (3) in the presence of the lithium compound (4) is usually carried out under an inert gas atmosphere such as argon, nitrogen or the like.

The reaction can be carried out without solvent or in an inert solvent, and examples of the solvent include, for example, a halogenated hydrocarbon such as 1,2-dichloroethane or the like, an aliphatic hydrocarbon such as hexane, heptane, octane, nonane or the like, an aromatic hydrocarbon such as benzene, toluene, xylene, chlorobenzene or the like, an ether such as diethyl ether, tetrahydrofuran or the like.

An amount of the solvent that may be used can be optionally set within an appropriate range to perform the reaction. It is usually 1 to 100 parts by, preferably 1 to 10 parts by weight per 1 part by weight of the alcohol compound of formula (3).

The reaction of the present invention can be carried out by contacting the ester compound of formula (2) with the alcohol compound of formula (3) and the lithium compound of formula (4), and typically it is conducted in such a way that the alcohol compound of formula (3) or a solution thereof in the solvent as described above is added dropwise at a suitable reaction temperature to a solution of the ester compound of formula (2) and the lithium compound of formula (4) in the solvent, alternatively the alcohol compound of formula (3), the ester compound of formula (2) and the lithium compound of formula (4) may be added, each independently as they are or in a solution form, to a reactor at one time and reacted at a suitable temperature.

During the reaction, an alcohol (e.g. lower alky alcohol such as methanol, ethanol or the like) derived from cyclopropanecarboxylate (2) is preferably removed from the reaction system continuously as a distillate fraction containing the alcohol. For example, the removal of the alcohol or alcohol-rich fraction can be made by conducting the reaction at a suitable temperature, for example, at a temperature higher than the boiling point of the alcohol formed during the reaction. It can also be accomplished by continuously or intermittently adding the solvent that forms an azeotrope with the alcohol that is formed in the reaction system with the progress of the reaction to withdraw an azeotropic distillate fraction. Alternatively, the distillate fractions above may be treated with an appropriate molecular sieve. In addition, the azeotropic distillate fraction may be separated by rectification, with a suitable rectification column, into its component alcohol or alcohol-rich fraction and the solvent fraction, which solvent may be returned to the reaction system to recycle it, thereby the reaction equilibrium may be effectively shifted toward the desired product.

The reaction temperature is not particularly restricted, and is usually in the range of 20 to 200° C., preferably 70 to 200° C.

A suitable amount (e.g. catalytic amount) of 4-(dimethylamino)pyridine, tetrabutylammonium bromide or 2,6-di-t-butyl-4-methylpheonol may be added in the present reaction.

After completion of the reaction, the ester compound of formula (1) can be isolated by washing the reaction mixture with water or an aqueous acidic solution, and an aqueous alkaline solution, if necessary, and concentrating. The isolated product may be further purified by distillation or chromatography or the like. Alternatively, the reaction mixture after completion of the reaction may be washed with water, and an aqueous alkaline solution, if necessary, to give an organic phase containing the product, which may be then mixed with water and heated to remove water and a solvent used, thereby providing the desired ester compound of formula (1).

EXAMPLES

The present invention is further explained by the following examples, which are not to be construed to limit the invention thereto.

Example 1

Into a 200 ml three-necked flask were added 35.7 g of xylene and 4.0 ml of 1.0 M solution of lithium methoxide in methanol (containing 152 mg of lithium methoxide) and methanol was distilled off by heating at 100° C. To the resulting solution were added 17.85 g of methyl 2,2-dimethyl-3-(2,2-dichlorovinyl)cyclopropanecarboxylate, 16.02 g of 3-phenoxybenzyl alcohol and the mixture was heated at 145° C. for 12 hours under reflux and stirring. After completion of the reaction, no coloring was observed for the reaction product, which was then analyzed by gas-chromatography to show that the yield of (3-phenoxyphenyl)methyl 2,2-dimethyl-3-(2,2-dichlorovinyl)cyclopropanecarboxylate was 94% in terms of the starting ester compound. The yield of by-product (3-phenoxyphenyl)methyl 2,2-dimethyl-3-(2-chloroethinyl)cyclopropane-carboxylate was 0.1%.

Comparative Example

An experiment was conducted in a similar manner as in Example 1 except that 771 mg of a 28% solution of sodium methoxide in methanol (containing 216 mg of sodium methoxide) was used in place of lithium methoxide. After completion of the reaction, reaction mixture was reddish brown. The mixture was analyzed by gas-chromatography to show that the yield of (3-phenoxyphenyl)methyl 2,2-dimethyl-3(2,2-dichlorovinyl)cyclopropane-carboxylate was 81% in terms of the starting ester compound. The yield of by-product (3-phenoxyphenyl)methyl 2,2 -dimethyl-3-(2-chloroethinyl)-cyclopropanecarboxylate was 1.1%.

Example 2

Into a 1000 ml separable flask were added 78.1 g of methyl 1R-trans-2,2-dimethyl-3-(1-propenyl) cyclopropanecarboxylate (0.464 mol, E/Z=⅕, wherein E/Z ratio is a geometrical isomer ratio with respect to the double bond), 0,79 g (0.004 mol) of 2,6-di-t-butyl-4-methylphenol, 320 g of n-heptane, and 0.34 g of (0.009 mol) of lithium methoxide, and 80.0 g (0.357 mol) of melted 2,3,5,6-tetrafluoro-4-methoxymethylbenzyl alcohol and 160 g of n-heptane were added in parallel thereto over 4 hours at 104 to 105° C. while removing a distillate fraction at the temperature. The amount of the distillate removed by this operation was 161.5 g. The reaction mixture was further heated at the temperature for 7 hours under simultaneous addition of n-heptane, while a distillate fraction was removed. The amount of the distillate thus removed was 566.9 g. After cooling the reaction mixture, it was washed with 160 g of water thrice, 240 g of 5% aqueous sodium hydroxide solution twice, 160 g of water once, 80 g of 1% hydrochloric acid twice, and 80 g of water twice in this sequence. One portion (49.9 g) of the obtained organic layer (376.7 g, hereinafter referred to as "solution A") was concentrated to give 18.7 g of a residue. The residue was analyzed by gas-chromatography using internal standard method to show that the content of 2,3,5,6-tetrafluoro-4-methoxymethylbenzyl 1R-trans-2,2-dimethyl-3-(1-propenyl)cyclopropanecarboxylate was 85.9%, wherein E/Z ratio is a geometrical isomer ratio with respect to the double bond. Based on the analysis, the concentration of the "solution A" was found to be 32.2% and the yield of the desired compound in this reaction was found to be 94.2%.

326.7 g of the solution A was charged in a 1000 ml separable flask and solvent was removed therefrom at 105 to 123° C. at normal pressure. To the resulting residue was added 555 g of water at one time and a component that makes an azeotrope with water was distilled off for 7 hours at 85 to 107° C., and water was further removed under reduced pressure to give 107.0 g of 2,3,5,6-tetrafluoro-4-methoxymethylbenzyl 1R-trans-2,2-dimethyl-3-(1-propenyl)cyclopropanecarboxylate.

Gas-chromatography analysis of the product showed that the yield of the desired product, E/Z=1/9, wherein E/Z ratio is a geometrical isomer ratio with respect to the double bond) was 97,2% (recovery ratio from solution A was 98.9%).

Gas-chromatography analysis conditions

Column: DB-1, 0.53Φ×30 nm, thickness of membrane 1.5 μm.

Column Temperature: 70° C. (5 min)→Temperature was raised at a rate of 5° C. min→300° C.(10 min)

Injection Temperature: 270° C.

Detector(FID) Temperature 310° C.

Carrier Gas: Helium, flow rate: 5 ml/min

Sample amount: 1 μl

Internal Standard: p-terphenyl

Example 3

Into a 100 ml round-bottomed flask were added 10.0 g of methyl 1R-trans-2,2-dimethyl-3-(1-propenyl)cyclopropanecarboxylate (0.059 mol), 20 g of toluene and 0.098 g (0.0026 mol) of lithium methoxide, and 10.0 g (0.052 mol) of 2,3,5,6-tetrafluoro-4-methylbenzyl alcohol dissolved in 10 g of toluene was added thereto over 2 hours at 122 to 127° C., while removing a distillate fraction at the temperature. The reaction mixture was further heated at the temperature for 6 hours, while toluene was added dropwise to remove a distillate fraction at the temperature. After cooling the reaction mixture at an ambient temperature, it was washed with 13.7 g of 1% sulfuric acid once, and 10 g of water twice. The organic phase was dried over anhydrous magnesium sulfate and the filtrate was evaporated to give 17.9 g of 2,8,5,6-tetrafluoro-4-methylbenzyl 1R-trans-2,2-dimethyl-3-(1-propenyl)cyclopropanecarboxylate. Gas-chromatography analysis of the crude product showed that content of the desired product was found to be 90.0% and the yield of the desired product was found to be 94.7%.

Gas-chromatography analysis conditions

Column: DB-WAX, 0.53Φ×30 m thickness of membrane 1.5 μm.

Column Temperature: 50° C. (5 min)→Temperature was raised at a rate of 5° C./min→220° C.(15 min)

Injection Temperature: 220° C.

Detector(FID) Temperature: 240° C.

Carrier Gas: Helium, flow rate: 20 ml/min

Sample amount: 1 μl

Internal Standard: biphenyl

Example 4

Into a 100 ml round-bottomed flask were added 6.57 g of methyl 1R-trans-2,2-dimethyl-3-(2-methyl-1-propenyl)cyclopropanecarboxylate (0.034 mol), 20 g of n-heptane and 0.049 g (0.0013 mol) of lithium methoxide, and 5.0 g (0.026 mol) of 2,3,5,6-tetrafluoro-4-methylbenzyl alcohol dissolved by heating in 10 g of n-heptane was added thereto over 2 hours at 105 to 106° C., while removing a distillate fraction at the temperature. The reaction mixture was further heated at the temperature for 8 hours, while n-heptane was added dropwise to remove distillate fraction at the temperature. Thereafter the reaction mixture was concentrated to give crude 10.1 g of 2,3,5,6-tetrafluoro-4-methylbenzyl 1R-trans-2,2-dimethyl-3-(2-methyl-1-propenyl)cyclopropanecarboxylate. Gas-chromatography analysis of the crude product showed that content of the desired product was found to be 77.4% and the yield of the desired product was found to be 88.7%.

Gas-chromatography analysis conditions

Column: DB-WAX, 0.53Φ×30 m, thickness of membrane 1.5 μm.

Column Temperature: 50° C. (5 min)→Temperature was raised at a rate of 5° C./min→220° C.(15 mil)

Injection Temperature: 220° C.

Detector(FID) Temperature: 240° C.

Carrier Gas: Helium, flow rate: 20 ml/min

Sample amount: 1 μl

Internal Standard: biphenyl

Comparative Example 2

An experiment was conducted in a similar manner as in Example 3 except that 0.139 g of 28% sodium methoxide in methanol (containing 216 mg of sodium methoxide, 0,026 mol) was used in place of 0.098 g (0.26 mol) of lithium methoxide. 17.2 g of an oil product was obtained. Gas-chromatography analysis using Internal standard method of the crude product showed that the content of 2,3,5,6-tetrafluoro-4-methylbenzyl 1R-trans-2,2-dimethyl-3-(1-propenyl)cyclopropanecarboxylate was found to be 55.6% and the yield was 55.5% in terms of 2,3,5,6-terafluoro-4-methylbenzyl alcohol.

What is claimed is:

1. A method for producing a cyclopropanecarboxylate of formula (1):

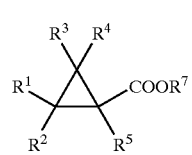

(1)

which comprises contacting a cyclopropanecarboxylate of formula (2):

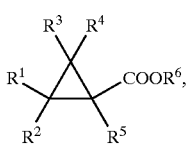
(2)

with a monohydroxy compound of formula (3):

R⁷OH    (3)

in the presence of a lithium compound of formula (4):

R⁸OLi    (4), wherein $R^1$, $R^2$, $R^3$, $R^4$ and $R^5$ each independently represent
a hydrogen atom, a halogen atom,
a substituted or unsubstituted alkyl group,
a substituted or unsubstituted alkenyl group, or
a substituted or unsubstituted aryl group;
$R^6$ represents an alkyl group having 1 to 10 carbon atoms or a substituted or unsubstituted phenyl group;
$R^7$ and $R^8$ do not simultaneously represent the same and each independently represent
a substituted or unsubstituted alkyl group, or
a substituted or unsubstituted aryl group.

2. The method according to claim 1, wherein $R^1$, $R^2$, $R^3$, $R^4$ and $R^5$ each independently represent:
a hydrogen atom, a halogen atom,
a substituted or unsubstituted straight, branched or cyclic alkyl group having 1 to 10 carbon atoms, which alkyl group may be optionally substituted with a group selected from:
 a halogen atom, a (C1–C3)alkoxy group,
 a (C1–C5)alkoxylcarbonyl group, a (C1–C5) alkylsulfonyl group
 and a (C1–C3)alkoxyimino group;
a (C2–C5)alkenyl group optionally substituted with a group selected from a halogen atom, a phenyl group,
 a (C1–C5)alkoxycarbonyl group which may be substituted with a halogen atom, a (C1–C5)alkylsulfonyl group,
 a (C1–C3)alkylsulfonyloxy group and a (C1–C3) alkoxyimino group, and a hydroxysulfenyl group;
a phenyl- or naphthyl-substituted (C1–C2)alkyl group which may be optionally substituted with a group selected from a (C1–C10)alkyl group and a (C1–C6) alkoxy group; or
a phenyl or naphthyl group which may be optionally substituted with a (C1–C10)alkyl group, a (C1–C10) alkoxy group or a halogen atom;
$R^6$ represents:
an alkyl group having 1 to 10 carbon atoms or
a phenyl group which may be optionally substituted with a group selected from (C1–C10)alkyl group and (C1–C10)alkoxy group or a halogen atom;
$R^7$ represents:
a (C1–C10)alkyl group which may be optionally substituted with a group selected from:
 a halogen atom,
 a (C3–C4)alkenyl group which may be substituted with a halogen atom,
 a (C3–C4)alkynyl group,
 a (C5–C6)cycloalkyl group,
 a (C5–C6)cycloalkenyl group,
 a heterocyclic group selected from:
  a furyl group which may be substituted with a phenoxy group, a benzyl group, difluoromethyl group or a propynyl group,
  a pyrrolyl group substituted with a propynyl group and optionally with a halomethyl group,
  a thiazolyl group substituted with a halomethyl group or a halomethoxy group,
  an isoxazolyl group optionally substituted with a methyl group,
  a 4,5,6,7-tetrahydroisoindol-1,3-dione-2-yl group,
  a 1-propynyl-imidazolidine-2,4-dione-3-yl group,
  a pyrazolyl group substituted with a propynyl group and a halomethyl group,
  a halo-pyridyl group,
  a thiazolin-2-one-5-yl group substituted with a methyl group and a propynyl group, and
  a 1-prop-2-ynylindol-3-yl group substituted with a methyl or trihalomethyl group;
 a (C5–C6)oxocycloalkenyl group substituted with a methyl group and either a propynyl group or a propenyl group;
 a phenyl-, naphthyl-, or anthracenyl-substituted (C1–C4) alkyl group, which phenyl-, naphthyl-, or anthracenyl group may be optionally substituted with a group selected from:
  a nitro group, a cyano group, a halogen atom,
  a (C1–C14)alkyl group which may be substituted with a halogen atom,
  a (C1–C3)alkoxy group which may be substituted with a halogen atom,
  a (C1–C4)alkoxy(C1–C3)alkyl group which may be substituted with a halogen atom,
  a (C2–C3)alkenyl group which may be substituted with a halogen atom,
  a (C3–C5)alkynyl group, a haloacetyloxy(C1–C3)alkyl group,
  a (C1–C3)alkylthio group which may be substituted with a halogen atom,
  an amino group, a thienyl group, a phenyl group, and a phenoxy group which may be substituted with a halogen atom, and
 said (C1–C4)alkyl group may form an indanyl group with the phenyl group; or
 a phenyl or naphthyl group which may be optionally substituted with a group selected from a halogen atom, a (C1–C10)alkyl group, a (C1–C10)alkoxy group, a (C3–C5)alkynyl group, an acetyl group and an aldehyde group.

3. The method according to claim 1 or 2, wherein $R^8$ represents a C1 to C10 alkyl group.

4. The method according to claim 3, wherein $R^6$ represents a methyl or ethyl group in formula (2).

5. The method according to claim 1, wherein the cyclopropanecarboxylate of formula (2) is 2,2-dimethyl-3-(2,2-dichlorovinyl) cyclopropanecarboxylate.

6. The method according to claim 1 or 2, wherein the cyclopropanecarboxylate of formula (2) is 2,2-dimethyl-3-(2-methyl-1-propenyl)cyclopropanecarboxylate.

7. The method according to claim 1 or 2, wherein the cyclopropanecarboxylate of formula (2) is 2,2-dimethyl-3-(1-propenyl)cyclopropanecarboxylate.

8. The method according to claim 1, wherein the monohydroxy alcohol of formula (3) is a primary alcohol.

9. The method according to claim 7, wherein $R^7$ represents a substituted or unsubstituted benzyl group, which phenyl group may be substituted with a group selected from:
- a halogen atom,
- a (C1–C14)alkyl group which may be substituted with a halogen atom,
- a (C1–C3)alkoxy group which may be substituted with a halogen atom,
- a (C1–C4)alkoxy(C1–C3)alkyl group which may be substituted with a halogen atom,
- a (C2–C3)alkenyl group which may be substituted with a halogen atom,
- a (C3–C5)alkynyl group, a haloacetyloxy(C1–C3)alkyl group,
- a (C1–C3)alkylthio group which may be substituted with a halogen atom,
- an amino group, a thienyl group, a phenyl group, and
- a phenoxy group which may be substituted with a halogen atom.

10. The method according to claim 8, wherein the monohydroxy compound of formula (3) is 3-phenoxybenzyl alcohol.

11. The method according to claim 1 or 2, wherein $R^1$ represents a methyl group, or a (C3–C4)alkenyl group, $R^2$ represents a hydrogen atom, or a methyl groups $R^3$ and $R^4$ represent a methyl group, $R^5$ represents a hydrogen atom, $R^6$ represents a methyl group or an ethyl group, and the monohydroxy compound is a compound of formula (5):

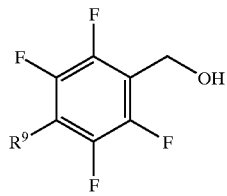

(5)

wherein $R^9$ represents
- a hydrogen atom, a halogen atom,
- a (C1–C3)alkyl which may be substituted with a halogen atom,
- a (C2–C3)alkenyl group which may be substituted with a halogen atom,
- a (C1–C3) alkoxy group which may be substituted with a halogen atom,
- a (C1–C3) alkylthio group which may be substituted with a halogen atom, or
- a (C1–C4alkoxy)methyl group which may be substituted with a halogen atom; and $R^8$ represents a (C1–C4)alkyl group.

12. The method according to claim 11, wherein the benzyl alcohol of formula (5) is added to a mixture of the ester compound of formula (2) and lithium compound of formula (4).

13. The method according to claim 10, wherein a hydrocarbon is used as a solvent.

14. The method according to claim 10, wherein $R^1$ represents a (C3–C4)alkenyl group, and $R^2$ represents a hydrogen atom.

15. The method according to claim 14, wherein $R^1$ is a 2-methyl-1-propenyl group or a 1-propenyl group.

16. The method according to claim 1, wherein $R^8$ represents a methyl or ethyl group.

* * * * *